United States Patent [19]
Kluger et al.

[11] Patent Number: 5,811,521
[45] Date of Patent: Sep. 22, 1998

[54] MULTIFUNCTIONAL CROSSLINKING REAGENTS FOR HEMOGLOBIN, AND CROSSLINKED HEMOGLOBIN CONJUGATES

[76] Inventors: Ronald H. Kluger, 14 Bradgate Road, Don Mills, Ontario, Canada, M3B 1J7; Krisztina Paal, Barthl-Mayer-Weh 5, D-85386 Eching, Germany

[21] Appl. No.: 793,087

[22] PCT Filed: Jun. 14, 1996

Related U.S. Application Data

[60] Provisional application No. 60/000,210 Jun. 16, 1995.

[86] PCT No.: PCT/CA96/00410

§ 371 Date: Apr. 11, 1997

§ 102(e) Date: Apr. 11, 1997

[87] PCT Pub. No.: WO97/00236

PCT Pub. Date: Jan. 3, 1997

[51] Int. Cl.$^6$ .............. A61K 35/14; C07K 1/00
[52] U.S. Cl. .......... 530/385; 530/350; 530/402; 530/410; 514/6
[58] Field of Search .................. 530/385, 350, 530/402, 410; 514/6

[56] References Cited

U.S. PATENT DOCUMENTS 5,250,665 10/1993 Kluger et al. ............ 530/385
5,399,671 3/1995 Kluger et al. ............ 530/385

OTHER PUBLICATIONS

Kluger et al, *J. Am. Chem. Soc.*, vol. 114, No. 24, pp. 9275–9279, 1992.

Paal et al, *J. Am. Chem. Soc.*, vol. 118, No. 43, pp. 10380–10383, 1996.

*Primary Examiner*—Cecilia J. Tsang
*Assistant Examiner*—Abdel A. Mohamed
*Attorney, Agent, or Firm*—Nixon & Vanderhye

[57] ABSTRACT

Multifunctional chemical reagents useful in cross-linking hemoglobin and having the capability of leaving two or more reaction sites available for further chemical reactions, after completion of the cross-linking process. These reagents are broadly defied as aromatic compounds comprising an aromatic nucleus including but not limited phenyl, biphenyl, naphthyl and binaphthyl, with at least four independently selected electronegative substituent groups bonded directly or indirectly to the aromatic nucleus.

18 Claims, 3 Drawing Sheets

BTDS

MULTIFUNCTIONAL CROSSLINKING REAGENTS FOR HEMOGLOBIN, AND CROSSLINKED HEMOGLOBIN CONJUGATES

This application claims benefit of USC Provisional Appln. No. 60/000,210 filed Jun. 16, 1995.

FIELD OF THE INVENTION

This invention relates to crosslinking reagents for proteins such as hemoglobin, and more particularly to chemical crosslinking reagents having a plurality of reactive sites, some of which react with globin chains of hemoglobin to effect crosslinking therebetween, and others of which remain available, after such crosslinking, for further reaction. From another aspect, the present invention relates to crosslinked hemoglobin conjugates, in which other groups or molecules, e.g. biomolecules, are chemically bonded to crosslinked hemoglobin.

BACKGROUND OF THE INVENTION AND PRIOR ART

Proposals have been made in the past to take advantage of the bioacceptability of hemoglobin, and its ability to circulate through the body in the bloodstream, as a drug delivery aid. Thus it has been proposed to prepare conjugates of hemoglobin with biologically active materials, and to inject such conjugates into the body, for therapeutic purposes. The biologically active material is assumed to remain biologically active when conjugated to the hemoglobin, or to be released from the hemoglobin in biologically active form after administration to and circulation through the body.

Site-directed cross-linking reagents for the specific modification of human hemoglobin have been developed and reported previously. The cross-linked protein can potentially be used as a red cell substitute and also as a carrier in bioconjugation. Cross-linkers with structurally defined bridging moieties and highly selective reaction sites can produce specifically defined linkages in the protein. This permits altered properties of the modified protein to be clearly related to its structure.

Thus U.S. Pat. No. 5,250,665 Kluger and Wodzinska, issued Oct. 5, 1993, discloses that crosslinking reagents such as trimesoyl tris(methyl phosphate) react with deoxy hemoglobin at the α-amino group of β-val 1 and the ε-amino group of lys 82 of both β-subunits, thereby utilizing all of the functional groups of the crosslinking reagent in hemoglobin crosslinking.

While common cross-linking reagents have two reaction sites, we have shown that a reagent with three reaction sites can cross-link a protein with great efficiency and novel utility. Once two sites on the cross-linker have reacted, the third site may react with a group on a protein or remain available for reaction with exogenous reagents.

Thus U.S. Pat. No. 5,399,671 Kluger and Song, issued Mar. 21, 1995, discloses that, in contrast with the teachings of Kluger and Wodzinska above, demonstrates that a reagent with three reaction sites can cross-link a protein with great efficiency and novel utility, but that once two sites on the trifunctional crosslinker have reacted, the third site may react with a group on a protein or remain available for reaction with exogenous reagents. The outcome depends on the functional group of the cross-linker. Reagents such as trimesoyl tris(3,5-dibromosalicylate) (TTDS) reacts only at β-lys 82 of the two β subunits, leaving the third ester group available reaction with added nucleophiles, and thereby providing a basis for bioconjugation and delivery of bioactive materials to the bloodstream of patients.

International Patent Application PCT/US92/09713 Somatogen Inc., published May 13, 1993, describes conjugates of human hemoglobin with various biological molecules, and proposes the use of such conjugates as drug carriers for drug delivery to the human body. The conjugates of this patent utilize cysteine residues, notably genetically engineered cysteine residues, on the globin chains of the hemoglobin, as coupling sites for the biological molecules to be carried, thereby effecting modification of the globin chains of the hemoglobin molecule.

The present invention has, as one objective, the provision of novel crosslinking agents for preparing crosslinked hemoglobin capable of conjugation to other biomolecules, and the provision of processes for preparation of such crosslinking reagents.

Another object of the present invention is the provision of a more efficient bioconjugation process whereby a relatively greater number of biomolecules may be conjugated to crosslinked hemoglobin, and the provision of novel products resulting therefrom.

SUMMARY OF THE INVENTION

The present invention, from one aspect, presents a crosslinked protein having a plurality of additional conjugation reaction sites available, derived from the residues of the crosslinking reagent. Thus, there are provided multifunctional chemical reagents useful in crosslinking proteins but having the capability of leaving two or more reaction sites available for further chemical reactions, after completion of the cross-linking process. These reagents can be broadly defined as aromatic compounds comprising an aromatic nucleus including but not limited to phenyl, biphenyl, naphthyl and binaphthyl (as hereinafter defined), with at least four independently selected substituent groups bonded directly or indirectly to the aromatic nucleus, each substituent group corresponding to the general formula I:

in which: X represents a direct bond, an ethylene group or an —NH— group;

Y represents —O—, —S— or a direct bond;

z represents one or more independently selected electronegative groups exhibiting positive Hammett sigma values;

and n is an integer from 1 to 5.

From another aspect, the present invention provides a process for preparing crosslinked hemoglobin having two or more free functionalities on the residue of the crosslinking agent available for subsequent conjugation to exogenous nucleophiles, which comprises reacting hemoglobin with a crosslinking reagent as defined above, under appropriate reaction conditions, and recovering the crosslinked hemoglobin so formed.

From a further aspect, the present invention provides conjugates of crosslinked hemoglobin and nucleophilic compounds, comprising:

hemoglobin crosslinked between globin chains by covalent coupling with a chemical crosslinking reagent, said crosslinking reagent having at least four active chemical sites available for reaction with nucleophiles;

at least one nucleophilic compound chemically covalently bonded to the residue of said chemical crosslinking agent;

at least two of the active chemical sites being utilized in the hemoglobin crosslinking and at least two others of the active chemical sites being utilized in covalent bonding to said at least one nucleophilic compound.

BRIEF REFERENCE TO THE DRAWINGS

DESCRIPTION OF THE PREFERRED EMBODIMENTS

The protein with which the reagents of the present invention are reacted is preferably hemoglobin, especially human hemoglobin, and so the invention will be described hereinafter with specific reference to crosslinking of hemoglobin, although it is applicable also to other, similar proteins.

Preferred crosslinking reagents according to the invention are those in which the substituted phenyl groups are linked to the aromatic nucleus through carboxy linkage, i.e., wherein group Y in Formula I is —O—. Examples of suitable groups Z are acetamido (at the ortho or meta positions), acetoxy, acetyl, carbomethoxy, carboxy, halo, cyano, ethoxy (at the ortho or meta positions), hydroxy (at the ortho or meta positions), methanesulfonyl, methoxy (at the ortho or meta position), nitro, phenyl, trifluoromethyl and trimethylammonio. Preferred as substituent group Z in Formula I are carboxyl, phosphonate, sulfonate, sulfate, phosphinate and halogen. Two or three such substituents are preferred, and especially cases where one of the substituents is carboxyl. When only one such substituent is present, it is preferred that it is located in the position ortho to the ester linkage to the aromatic nucleus.

The terms biphenyl and binaphthyl as used herein in connection with the aromatic nucleus of the crosslinking reagents encompass aromatic nuclei comprising two phenyl groups or two naphthyl groups, linked to one another directly or through the intermediary of an alkylene group —(CH$_2$—CH$_2$)$_n$— or an alkylene-oxy group —(CH$_2$—CH$_2$—O)$_n$—, where n is an integer of from about 1 to 8. An especially suitable aromatic nucleus is biphenyl with the phenyl groups directly linked.

The particularly preferred crosslinking agents for use in the present invention are those which specifically crosslink hemoglobin, consistently and reproducibly, at specific, predetermined sites on the globin chains. In this way, one can reliably obtain a product with known, reproducible structure and properties each time the crosslinking agent is used, often a necessary precondition for the preparation of products to be used in biochemical applications.

Figure 1:
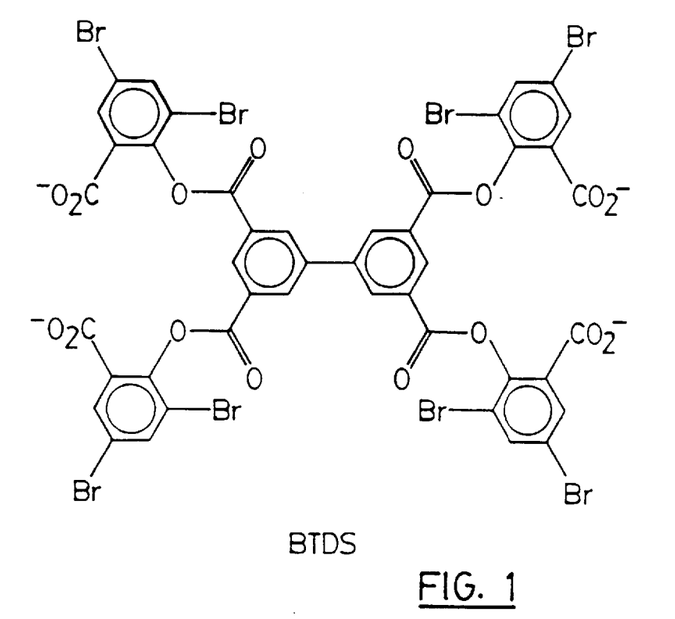
FIG. 1 is the structural formula of a first, specific, novel crosslinking reagent according to the invention, namely 3,5,3',5'-biphenyltetracarbonyl tetrakis(3,5-dibromosalicylate), prepared according to Example 1 hereof, and hereinafter sometimes referred to as BTDS.

One class of preferred crosslinking reagents according to the invention comprises 3,5-dibromosalicyl esters of tetrahexacarboxylic acids. A specific such compound is (3,5,3', 5'-biphenyltetracarbonyltetrakis(3,5-dibromo-salicylate; BTDS), the structure of which is illustrated in FIG. 1 of the accompanying drawings. The present invention also provides a synthesis of this novel material and a process of reacting it with hemoglobin to produce a crosslinked protein with two reaction sites, with high efficiency.

Figure 6:
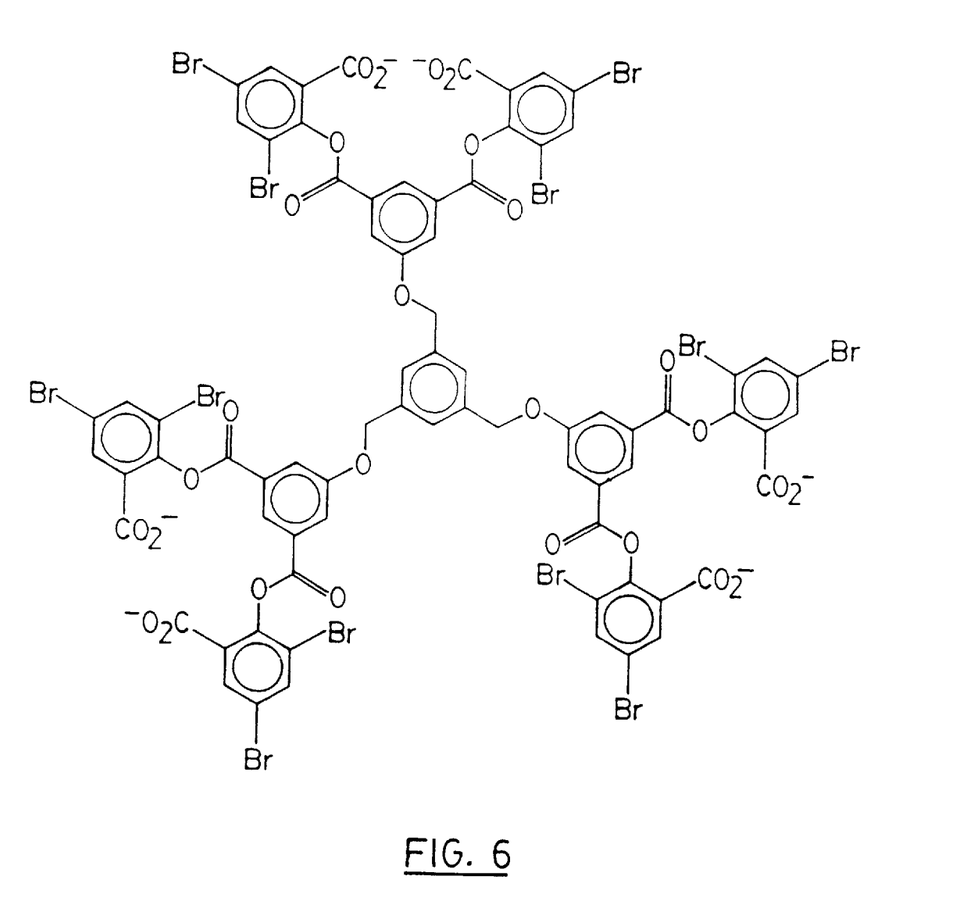
FIG. 6 is the structural chemical formula of a hexafunctional crosslinking reagent of the present invention, the product of Example 6 below, namely 1,3,5-tris{[3,5-bis(dibromosalicyloxycarbonyl)phenoxy]methyl} benzene.

An analogous reagent providing a multiplicity of such reaction sites available after crosslinking of hemoglobin, has been effected, and providing even more efficient bioconjugation and drug delivery, is illustrated in FIG. 6 of the accompanying drawings.

In these compounds, the illustrated bromine substituents are readily replaceable, wholly or partially, and at other positions of the respective phenyl rings, with other electronegative groups selected from those referenced above for group Z, and which, at the position on the phenyl ring at which they are substituted, exhibit positive Hammett sigma values.

This technology can be further extended to prepare crosslinkers which, when reacted with hemoglobin, give modified hemoglobins in which the added entity is derivatized with any number of reactive groups. Appropriate substitution of the crosslinker can be used to generate modified hemoglobin in which one or more sites on each of two or more of the globin chains are linked. These crosslinkers may be used in combination with others to provide hemoglobin crosslinked at more than one site, with one or more of the linkages presenting reactive groups.

Suitable methods of preparing crosslinking reagents according to the present invention can be based upon Collman's procedure, see Coleman et.al.; (1988) *J. Am. Chem. Soc.*, 110, 3483. According to this procedure, a diihodoethane compound, for example 1,2-bis(iodoethoxy) ethane, may be reacted with a hydroxy-substituted aromatic diester such as diethyl 5-hydroxyisophthalate to replace the iodo groups with aromatic diester groups, thereby forming a tetraester with a nucleus of linked aromatic groups such as polyether-linked phenyl groups. The tetraester can be hydrolyzed to the tetra-acid, and converted to the tetracarbonyl chloride by reaction with thionyl chloride. By reaction of this tetracarbonyl chloride with four equivalents of the potassium salt of a phenol substituted with appropriate substituents Z as defined in connection with formula I, for example the potassium salt of t-butyl 3,5-dibromosalicylate, one can prepare the compounds according to the invention. This procedure is a modification of that described by Klotz and coworkers[5].

The hemoglobin is preferably reacted with the crosslinking reagent in its deoxy form and under conditions which include the substantial absence of oxygen. The hemoglobin can, in the alternative, be reacted whilst in other protected forms such as carbon monoxylated Hb, but lower yields of crosslinked Hb are thereby obtained.

Crosslinking reagents according to the present invention having six or more reactive groups and leaving three or more free functionalities available for conjugation after the reaction with hemoglobin can, in one aspect, be regarded as dendrimers and prepared by methods of organic chemistry analogous to those proposed previously for dendrimer formation. Dendrimers are polyfunctional multibranched molecules. The number of functional groups of these compounds can easily be multiplied through several reaction steps. Two different methods have been developed for the preparation of dendrimers. The molecule is either extended on a polyfunctional core (divergent route), or polyfunctional building blocks are prepared separately and attached to the core in a final reaction step (convergent route). Cross-linking hemoglobin with multifunctional reagents, such as dendrimers, provides another route for the introduction of a large number of novel reaction sites into the protein. A few of the functional groups normally two, participate in crosslinking the hemoglobin, and the rest can be utilized for further modification of the hemoglobin, e.g. conjugation. FIG. 6 of the accompanying drawings illustrates the chemical structure of one such dendrimer, a compound having a biphenyl nucleus with the phenyl groups linked through an ethylene-oxy linkage, and carrying six functional, dibromo-salicylate groups, linked to the aromatic, biphenyl nucleus through ester linkages and, in respect of two of the functional groups, additionally through a phenyl-ethylene-oxy linkage.

Conjugates according to the present invention in general comprise covalently bonded conjugates of crosslinked hemoglobin as discussed above, with exogenous nucleophilic molecule, suitably biomolecules, in which at least two residual functional groups from the crosslinking reagent are utilized to bond to the exogenous nucleophile. There may be two or more such nucleophilic molecules, the same or different, bound to each crosslinked hemoglobin molecule, with each such nucleophilic molecule having a single covalent link to the crosslinking reagent residue, i.e. using a single one of the active site not involved in the hemoglobin crosslink. Alternatively, a single nucleophile molecule may be bound to the crosslinking reagent residue by means of two or more of these active sites.

The conjugates according to the invention can be prepared by reaction of the two or more functionalities of the crosslinking reagent not required or used in the hemoglobin crosslinking reaction, with appropriate groups of the exogenous nucleophilic compound either before or after the crosslinking of hemoglobin therewith is undertaken.

Preferred exogenous compounds for forming conjugates according to the present invention have primary, or secondary amine groups available for reaction with the residual active sites on the crosslinking reagents. The compounds may be pharmaceutical compounds, which retain their pharmaceutical activity whilst covalently coupled to the crosslinked hemoglobin, or which are released in the body in a pharmaceutically active form.

The reaction conditions to be observed in forming conjugates according to the invention include temperatures and reaction environments commonly used in hemoglobin chemistry, designed to ensure that the basic, desired properties of the hemoglobin are retained in the final product. For example, temperatures and other conditions which avoid denaturing the hemoglobin need to be observed. These are within the skill of the art.

Specific examples of conjugants reactable with the crosslinked hemoglobin according to the present invention include the following:

amino acid conjugants wherein an amino acid such as lysine, glycine, phenylalanine and the like is covalently bonded to the crosslinking reagent residue via its amino group;

polyhydroxylamines such as Bis-Tris, of formula:

in which two or more hydroxyl groups will bond to the crosslinking reagent residue, leaving additional hydroxyl groups available for further reaction with other exogenous compounds;

peptides and polypeptides such as in which the primary amino group bonds to the crosslinking reagent residue;

enzyme cofactor analogs such as pyridinium nucleotide analog:

biotinyl hydrazide:

FMN analog:

in each of which the primary amine group will react with the crosslinking reagent residue;

hormones such as norepinephrine:

in which the primary amino group will react with the crosslinking reagent residue, and epinephrine:

in which the secondary amino group reacts with the crosslinking reagent residue;

haptens, coenzymes, nucleophilic group-containing drugs, saccharides, lipids and nucleic acids are other classes of compounds which can be coupled by covalent bonding to the crosslinking reagent, either before or after the crosslinking reagent is reacted with the hemoglobin to effect crosslinking.

In all of the above cases, each of the plurality of active sites on the crosslinker unused in the crosslinking of hemoglobin can be used for conjugation. Accordingly, each crosslinked hemoglobin molecule can be conjugated to two or more molecules of the same or different conjugants. Alternatively, a single molecule of a conjugant having two or more reactive groups may link to the crosslinking residue with two covalent bonds, to provide a novel composition.

Bioconjugates of crosslinked hemoglobin and drug molecules according to the present invention can increase the circulating half-life of the drug in the body system, as a result of increased molecular weight. The hemoglobin may afford a degree of protection of the drug against premature metabolism, thereby providing improved stability. The hemoglobin-drug conjugates of the present invention in many cases have reduced or masked lipophilicity so that the drug is not rapidly cleared to fatty deposits. Consequently, fewer administrations of the drug may be required, along with smaller total quantities of drug to have the same therapeutic effect. The toxicity of drugs may be blocked until the conjugate is delivered to the target site, thereby preventing non-specific toxicity. Improved drug solubility may also result from the conjugation of the drug to the water soluble, crosslinked hemoglobin. Hemoglobin as a carrier may also decrease or prevent toxicity at the normal site of metabolism or clearance of the conjugant, i.e. by limiting the metabolism of Hb-conjugates to the site of metabolism of native, unmodified Hb. In this way, Hb-conjugates will not only provide targeting to the site of desired drug action, but also to the site of final metabolism of Hb, and away from sites of toxic reaction.

The crosslinked hemoglobin according to the invention retains its oxygen carrying capability, to a very large extent, even after bioconjugation. Accordingly, conjugates comprising the crosslinked hemoglobin conjugated to a chemotherapeutic requiring oxygen (e.g. phosphamides, adriamycin, nitrosoureas and the like) form a particularly advantageous embodiment of the present invention.

In addition, the hemoglobins of the present invention can be conjugated to colloids with multiple reactive groups such as polyamines and polyhydroxyls (e.g. polylysine, aminopolysaccharides, amine-derivatized HETA-starch, dextrans). Such colloids will react with several hemoglobins crosslinked according to the present invention. They use unique attachment sites derived from the residue of the crosslinking reagent as described, and consequently are highly uniform and characterizable, with homogeneous oxygen binding properties. Such colloids have increased circulation times as a result of increased molecular weight, and provide products of altered viscosities, or predetermined concentration of hemoglobin per unit of colloid. The present invention thus enables the preparation of a hemoglobin-based oxygen carrier using less hemoglobin with an increased retention time while maintaining the same oncotic properties as the undiluted, non-conjugated form.

The invention is further described and illustrated in the following specific examples. All NMR spectra were recorded on a Varian Gemini (200 MHz) spectrometer.

EXAMPLE 1

Synthesis of 3,5,3',5'-Biphenyltetracarbonyl Tetrakis (3,5-dibromosalicylate), BTDS 1.41 g (4.0 mmol) of t-butyl 3,5-dibromosalicylate and 0.45 g (4.0 mmol) of potassium t-butoxide was stirred in 30 mL of anhydrous THF for 20 m. A solution of 0.40 g(1.0 mmol) of 3,5,3',5'-biphenyltetracarbonyl tetrachloride (prepared, from 3,5,3',5'-biphenyltetra-carboxylic acid, a known compound in the literature, synthesized from the commercially available 5-bromo-m-xylene, the tetracarbonyl tetrachloride being prepared by reaction with thionyl chloride and a catalytic amount of DMF) in 15 mL of anhydrous THF was added and stirring was continued overnight. Water was added to the mixture and the product was extracted with ether. The solution was dried over $MgSO_4$, filtered, and the solvent was evaporated. The white solid was dissolved in 20 mL of anhydrous trifluoroacetic acid, for deprotection, and was allowed to stand at room temperature for 1 h. Then 20 mL of ether was added to the solution producing a white precipitate which was filtered and dried in vacuum (1.1 g, 76%). IR (KBr) 3079 (br s, $v_{OH}$), 1736 (S, $v_{C=O}$) 1202 (s, $v_{C-O)\,cm}^{-1}$; $^1H$ NMR (dioxane-$d_8$) δ 9.01 (2 H, t, J=1.6 Hz, ArH), 8.80 (4 H, d, J=1.6 Hz, ArH), 8.21 (8 H, dd, J=4.0 Hz, ArH), 2.57 (4 H, br s, $CO_2H$); $^1H$ nmr (DIOXANE-$D_8$) δ 9.01 (2H, t,J=1.6 Hz), 8.80 (4H,d,J=1.6 Hz), 8.21(8H,dd,J=4.0 Hz), 2.57 (4H,brs); $^{13}C$ NMR (dioxane-$d_8$) δ 163.56, 162.96, 148.26, 141.65, 140.29, 134.85, 134.72, 131.85, 131.48, 127.55, 120.01; MS (negative FAB): 1441 (M-1) UV (dioxane) $\lambda_{max,1}$=230 nm, $\epsilon_{max,1}$=133,000, $\lambda_{max,2}$=296 nm, $\epsilon_{max,2}$=14,000.

EXAMPLE 2

Reaction of Deoxy-Hemoglobin with 3,5,3',5'-Biphenyltetracarbonyl Tetrakis (3,5-dibromosalicylate), BTDS.

2.0 mL of 1.40 mM COHb in 50 mM Bis-Tris buffer (pH 6.5) was passed through a Sephadex G-25 column equilibrated with 50 mM sodium borate buffer (pH 8.0). COHb was converted into its oxy form by irradiation under oxygen flow at 0° C. for 2 h. Oxy-Hb was deoxygenated under nitrogen at 38° C. for 2 h. 8 mg (0.0056 mmol) of the cross-linking reagent BTDS was dissolved in 1.0 mL of dioxane and 2.8 mL of 50 mM sodium borate buffer (pH 8.0) was added. The solution was deoxygenated under vacuum followed by addition of nitrogen three times. Then it was added to the deoxy-Hb solution anaerobically. The reaction mixture was kept at 38° C. for 2 h and nitrogen saturated with water flowed through the rotating flask continuously. At the end of the reaction period the flask was flushed with carbon monoxide. The solution of the modified Hb was passed through a Sephadex G-25 column equilibrated with 0.1 M MOPS buffer (pH 7.2) in order to separate the unreacted reagent.

The resulting product, (3,5-dibromosalicyl-biphenyltetracarbonyl-((Lys-β-82)-(Lys-β'-82))-hemoglobin, is hereinafter referred to as DBSB-Hb.

The reaction was run at several pH values (7.2, 8.0, 9.0). When the experiments were run with COHb, there was no formation of significant amount of modified protein at any pH. However, deoxy-Hb reacts with BTDS readily. Using 2 equivalents of the cross-linker at any of the above pH values, there was no unmodified Hb left in the reaction mixture. The best results were achieved at pH 8.0.

The peak corresponding to the cross-linked β subunits was separated on a C-4 reversed phase HPLC column and the material was identified by its ionspray mass spectrum. $M^+$: 32,585 (found), 32,586 (calc.). According to the C-4 reversed phase HPLC chromatogram (globin chain separation) the major product is about 95% of the mixture of modified hemoglobins formed during the cross-linking reaction.

EXAMPLE 3
Structure Determination of the Modified Hemoglobin

Globin chains were separated on a C-4 reversed phase HPLC column. Ionspray MS of the material corresponding to the major peak in the C-4 chromatogram shows that it is two β-chains cross-linked by the BTDS with the other two 3,5-dibromosalicylate groups unreacted.

Figure 3:
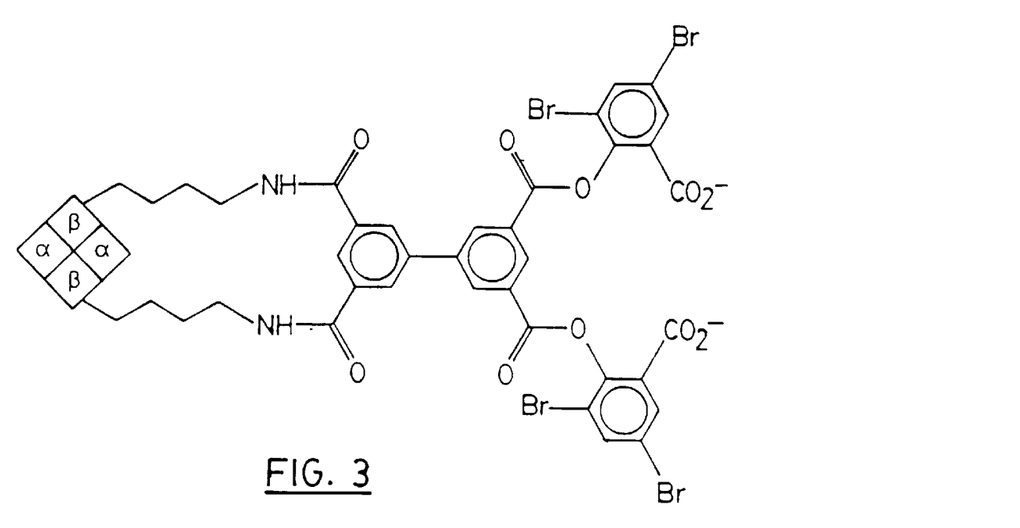
FIG. 3 is a diagrammatic illustration of the product of Example 3 below.

Globin chains were digested by trypsin followed by endoproteinase Glu-C. The resulting peptides were separated on a C-18 reversed phase HPLC column. Peptide patterns of modified and unmodified β-chains were compared in order to establish the site of modification. According to the results, the cross-link occurs between the Lys-82 residues of the two β subunits. The major product (3,5-dibromosalicyl-biphenyltetracarbonyl-((Lys-β-82)-(Lys-β'-82))-hemoglobin, hereinafter referred to as DBSB-Hb is illustrated in accompanying FIG. 3. According to the C-4 reversed phase HPLC chromatogram (globin chain separation) the major product is about 95% of the mixture of modified hemoglobins formed during the cross-linking reaction.

The peak corresponding to the cross-linked β subunits was separated on a C-4 reversed phase HPLC column and the material was identified by its ionspray mass spectrum. $M^+$: 32,585 (found), 32,586 (calc.).

As the above results show, BTDS is a highly specific acylating agent for the ε-amino groups of the Lys-82 residues of both β-chains of Hb. Its reaction with the deoxy form of the protein results in a cross-link between the two β subunits, giving DBSB-Hb in very good yield.

Since there are two possible ways for BTDS to form the linkage between the two Lys-82 residues of the β subunits, the exact structure of the product can be established by X-ray crystallography only. Based on previous results with the isophthalyl[2] and the trimesyl[4] cross-linking reagents however, BTDS is likely to participate in the cross-linking reaction with two of its active ester groups on the same benzene ring. DBSB-Hb presumably has the structure shown in FIG. 3, although the other possibility cannot be excluded.

EXAMPLE 4
Reaction of DBSB-Hb with Ethylene Diamine

The cross-linking procedure was carried out as described in Example 2. 1.0 mL of 1.17 mM CO-Hb in 5 mM tris buffer (pH 7.6) was used as starting material and the reaction was run at pH 8.0. At the end of the reaction period the reaction vessel was flushed with carbon monoxide. Then the solution of the modified hemoglobin was passed through a Sephadex G-25 column equilibrated with 50 mM pH 8.0 sodium borate buffer, in order to separate the unreacted reagent.

To the above solution, immediately afterwards, 230 μL of 2.0M solution (200-fold excess) of ethylene diamine adjusted to pH 8.0 with cc. HCl was added. The reaction vial was sealed and was kept at 37° C. for 2 h. Then the reaction mixture was passed through a Sephadex G-25 column equilibrated with 50 mM pH 8.0 sodium borate buffer, in order to separate the excess of the ethylene diamine.

Figure 4:
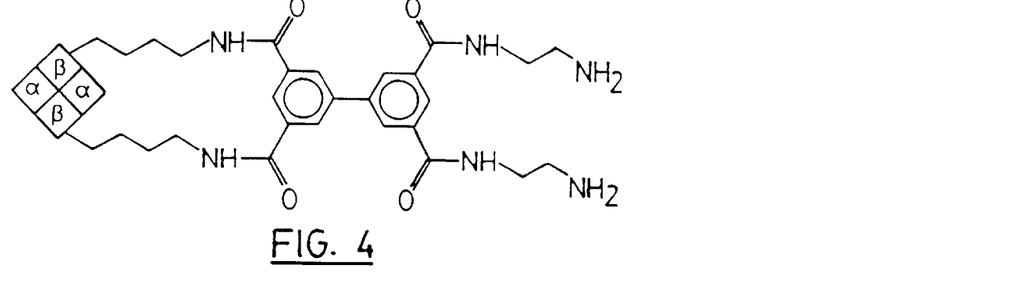
FIG. 4 is a diagrammatic illustration of the product of Example 4 below.

The high excess of ethylene diamine serves to minimize the extent of the competing hydrolysis of the 3,5-dibromosalicylate groups. The reaction was followed on a C-4 reversed phase HPLC column under conditions which separate the heme and the globin chains. The major new peak formed during the reaction was separated on a C-4 reversed phase HPLC column. The product was identified by using ionspray mass spectrometry: $M^+$ 32,109 (found), 32,114 (calc.). Ionspray mass spectrum of the material showed that it was two β subunits cross-linked with BTDS with two molecules of ethylene diamine attached to the cross-linker. The schematic structure of the product is shown in the accompanying FIG. 4.

It was successfully demonstrated that two molecules of a nucleophile can be attached to the two remaining reactive sites of BTDS in the cross-linked hemoglobin. This promises a future application of DBSB-Hb as a semi-natural drug carrier that in addition is twice as efficient as the DBST-Hb of the aforementioned Kluger et. al. patent.

EXAMPLE 5
Synthesis of 1,2 bis{2-[3,5bis(3,5-dibromosalicyloxycarbonyl)phenoxy]ethoxy}ethane (DPEE)

The target molecule was prepared from the tetracarbonyl tetrachloride according to the procedure of Klotz et al.[5]. The tetrakis(t-butyl 3,5-dibromosalicylate) formed in the reaction of the tetrachloride with t-butyl 3,5-dibromosalicylate. Deprotection with trifluroacetic acid gave the desired product.

Synthesis of the tetracarbonyl tetrachloride was achieved by modifying Collman's procedure[1]. Nucleophilic substitution of the iodines of 1,2-bis(2-iodoethoxy)ethane with diethyl 5-hydroxyisophthalate in anhydrous THF gave the tetraester, which was then purified on a silica column. Hydrolysis with excess sodium hydroxide in ethanol yielded the tetracarboxylic acid. The tetracarbonyl tetrachloride was prepared with thionyl chloride and catalytic amount of DMF.

Synthesis of the Tetraester. 952 mg (4 mmol) of diethyl 5-hydroxyisophthalate and 475 mg (4.25 mmol) of potassium t-butoxyde was stirred in 20 mL of anhydrous THF for 30 m. Then a solution of 740 mg (2 mmol) of 1,2bis(2-iodoethoxy)ethane in 20 mL of anhydrous THF was added and the reaction mixture was allowed to reflux for 48 h under nitrogen. Water was added and the product was extracted with ether. The solution was dried over $MgSO_4$, filtered, and the solvent was evaporated in vacuum. Purification on a silica column (hexanes-EtOAc 1:1) gave a white powder (0.60 g, 51%).

$^1$H NMR ($CDCl_3$)δ 8.25 (2H, t, J=1.2 Hz, ArH), 7.74 (4H, d, J=1.2 Hz, ArH), 4.36 (8H, q, J=6.9 Hz, $CH_2$), 4.20 (4H, t, J=5.6 Hz, $CH_2$), 3.87 (4H, t, J=5.6 Hz, $CH_2$) 3.75 (4H, s, $CH_2$), 1.36 (12 H, t, J=6.9 Hz, $CH_3$).

Synthesis of the Tetraacid. 0.60 g(1.0 mmol) of the tetraester was dissolved in 30 mL of ethanol and the solution was heated to 65° C. Then 0.25 g (6 mmol) of sodium hydroxide dissolved in 1 ml of water was added and the reaction mixture was kept at 65° C. for 22 h. The white precipitate that formed was filtered out and dissolved in 10 mL of water. The tetraacid was precipitated with HCl and it was filtered out. The product was dried under vacuum (0.46 g, 95%).

$^1$H NMR (DMSO-$d_6$) δ 8.05 (2H, s, ArH), 7.62 (4 H, s, ArH), 4.19 (4H, s, $CH_2$), 3.75 (4H, s, $CH_2$), 3.60 (4H, s, $CH_2$), a broad band is also present under the three high-field signals.

Synthesis of the Tetracarbonyl Tetrachloride. 225 mg (0.47 mmol) of the tetraacid was dissolved in 15 mL of thionyl chloride and three drops of DMF was added. The solution was refluxed under nitrogen for 5 h. The solvent was evaporated in vacuum. The product (yellowish oil) was dried under vacuum and solidified overnight. (260 mg, 100%). It was used without further purification.

$^1$H NMR ($CDCl_3$) δ 8.43 (2 H, t, J=1.6 Hz, ArH), 7.90 (4H, d, J=1.6 Hz, ArH), 4.24 (4H, t, J=5 Hz, $CH_2$), 3.89 (4H, t, J=5 Hz, $CH_2$), 3.74 (4H, s, $CH_2$).

Figure 2:
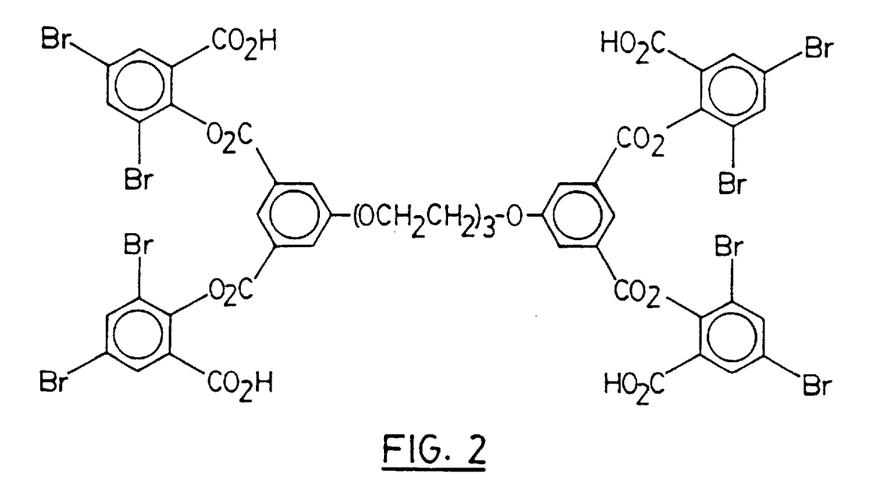
FIG. 2 is the structural formula of a second, specific, novel crosslinking reagent according to the invention, namely 1,2-bis{2-[3,5-bis(3,5-dibromosalicyloxy-carbonyl)phenoxy]ethoxy}ethane, prepared according to Example 5 hereof (DPEE)

Synthesis of the Tetrakis (3,5-Dibromosalicylate). 663 mg (1.88 mmol) of t-butyl-3,5-dibromosalicylate and 211 mg (1.88 mmol) of potassium t-butoxyde was stirred in 15 mL of anhydrous THF for 30 m. Then a solution of 260 mg (0.47 mmol) of the tetracarbonyl tetrachloride in 15 mL of anhydrous THF was added and the reaction mixture was stirred at RT overnight. Water was added and the product was extracted with ether. The solution was dried over $MgSO_4$, filtered, and the solvent was evaporated in vacuum. (White solid, 750 mg, 88%). This t-butyl protected compound was dissolved in 15 ml of anhydrous TFA and was allowed to stand at RT for 2.5 h. Then 15 mL of dry ether was added whereupon a white precipitate formed . It was kept at 4° C. overnight. The product was filtered out and dried in vacuum. (White powder, 550 mg, 84%). The chemical structure of the end product, 1,2-bis-{2-[3,5-bis-(3,5-dibromosalicyloxycarbonyl)phenoxy]-ethoxy}ethane, is shown in FIG. 2 of the accompanying drawings.

IR (KBr) 3177 (br s, $v_{OH}$), 1736 (s, $v_{C=O}$), 1195 (s, $v_{C-O}$) $cm^{-1}$; $^1$H NMR (DMSO-$d_6$) δ 8.36 (2 H, t, J=1.4 Hz, ArH), 8.33 (4 H, d, J=2.5 Hz, ArH), 8.09 (4 H, d, J=2.5 Hz, ArH), 7.98 (4 H, d, J=1.4 Hz, ArH), 4.31 (4 H, br s, $CH_2$), 3.79 (4 H, br s, $CH_2$), 3.63 (4 H, s, $CH_2$), a broad band is also present under the three highfield signals; $^{13}$C NMR (acetone-$d_6$) δ 163.57, 163.25, 160.59, 148.36, 140.13, 134.68, 131.79, 128.06, 124.54, 122.12, 120.29, 120.06, 71.50, 70.29, 69.47; MS (negative FAB): 1589 (found), 1589 (M-1 calcd. for $C_{50}H_{30}Br_8O_{20}$).

EXAMPLE 6

Synthesis of N,N'-trimesoylbis(3,5-dibromosalicylate) benzidine diamide

Figure 5:
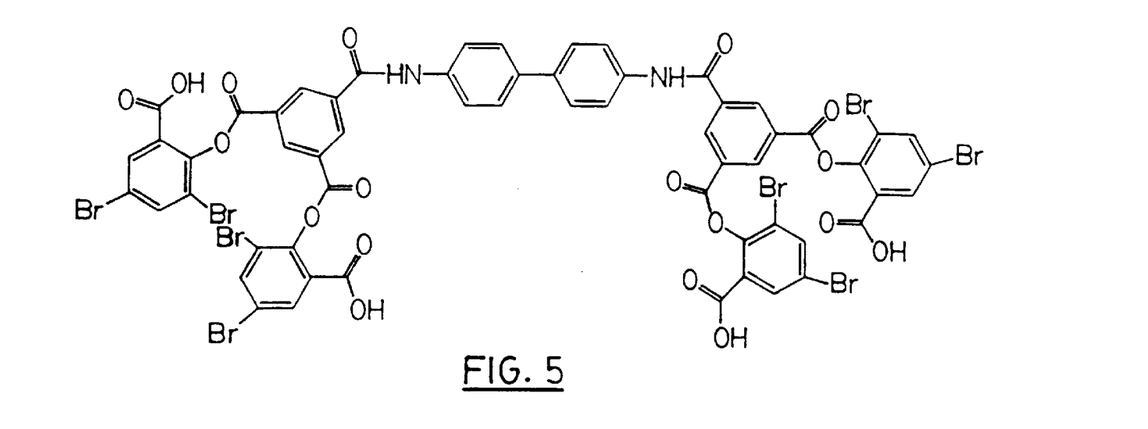
FIG. 5 is a diagrammatic illustration of the product of Example 6 below.

The structural chemical formula of this compound is illustrated in FIG. 5 of the accompanying drawings.

Trimesoyltris-1-(tert.butoxycarbonyl)-3,5-dibromosalicylate (t-BuTTDS), synthesized by the method of Kluger and Song, 0.96 mmole was dissolved in about 50 ml freshly distilled dry THF. Benzidine (87 mg, 0.5 mmol) and potassium tert-butoxide (155 mg, 1.4 mmol) were dissolved in 100 mL freshly distilled dry THF and added dropwise to a stirring solution of the t-BuTTDS at room temperature, under argon. A cloudy but colorless solution resulted. a stirring continued for 3 days. Cloudiness increased and the solution became light purple. The solution was evaporated to dryness and the residue was dissolved in 50 mL TFA in order to remove the protecting group. A clear reddish-brown solution resulted. Stirring continued for 2 hours upon which some yellowish precipitate appeared. Freshly distilled diethyl ether (50 ml) was added and the mixture was cooled in an ice bath for 30 min. The mixture was filtered by suction. An off-white solid was collected and dried in vacuum. $^1$H nmr is consistent with the desired product in pure form. FAB mass spectrometric analysis gave two species, consistent with the structure shown in FIG. 5 and the hydrolysis product thereof.

EXAMPLE 7

In this Example, a hexafunctional protein crosslinking reagent of the structural formula shown in FIG. 6, a dendrimer, was prepared by reaction of a hexacarboxylic acid, namely 1,3,5-tris [(3,5-dicarboxyphenoxy)methyl] benzene with a dibromosalicylate, namely t.butyl-3,5-dibromosalicylate, to esterify each of the carboxylic groups with 3,5-dibromosalicylate functional groups. The hexacarboxylic acid is prepared by reaction of 1,3,5-tris (bromomethyl)benzene with diethyl 5-hydroxyisophthalate (potassium salt) followed by hydrolysis.

Synthesis of 1,3,5-Tris (bromomethyl)benzene

The reaction was carried out according to the procedure of Vögtle[6]. After washing the filtrate and drying it over magnesium sulfate, the solvent was completely evaporated. The yellowish liquid obtained was purified on a silica column (hexanes-chloroform 3:1). According to the $^1$H NMR spectrum the product was a mixture of 1,3,5-tris(bromomethyl) benzene and 1-dibromomethyl-3,5-bis(bromomethyl) benzene in a 3:2 ratio. This mixture is a satisfactory starting material for the next stage of the synthesis.

Synthesis of 1,3,5-Tris{[3,5-bis(ethoxycarbonyl)phenoxy] methyl}benzene

Diethyl 5-hydroxyisophthalate (1.1 g, 0.0046 mol) was stirred with potassium t-butoxide (0.56 g, 0.0050 mol) in 70 mL of dry tetrahydrofuran at room temperature for 30 min. Then a solution of 0.55 g of the 3:2 mixture of the tri- and tetrabromo compounds (containing 0.30 g, 8.4×10$^{-4}$ mol of the tri-bromo compound) in 30 mL of dry tetrahydrofuran was added dropwise and the reaction mixture was continued to be stirred at room temperature for 48 h. Water was added and the products were extracted with ether. The solution was dried over magnesium sulfate, filtered, and ether was removed. Purification of the product on a silica column (3×30 cm, dichloromethane-acetone 100:3) yielded a white solid (0.37 g, 53%): $^1$H NMR ($CDCl_3$) δ 8.29 (3 H, s, ArH), 7.83 (6 H, s, ArH), 7.53 (3 H, s, ArH), 5.18 (6 H, s, $CH_2$), 4.39 (12 H, q, J=6.9 Hz, $CH_2$), 1.39 (18 H, t, J=6.9 Hz, $CH_3$,); MS (EI): 828.298 (found), 828.299 ($M^+$ calcd. for $C_{45}H_{48}O_{15}$)

Synthesis of 1,3,5-Tris[(3,5-dicarboxyphenoxy)methyl] benzene

The hexaethyl ester product from the previous step (0.23 g, 2.7×10$^{-4}$ mol) was dissolved in 135 mL of tetrahydrofuran and 35 mL of 0.1M sodium hydroxide was added. The reaction mixture was stirred at 50° C. overnight. Tetrahydrofuran was evaporated and the remaining solution was acidified with concentrated hydrochloric acid. A white precipitate formed. This was filtered and dried in vacuum (0.17 g, 97%): IR (KBr) 3016 (br s, $v_{OH}$), 1708 (s, $v_{C=O}$), 1272 (s, $v_{C-O}$) $cm^{-1}$; $^1$H NMR (DMSO-$d_6$) δ 8.09 (3 H, t, J=1.4 Hz, ArH), 7.76 (6 H, d, J=1.4 Hz, ArH), 7.60 (3 H, s, ArH), 5.30 (6 H, s, $CH_2$), −2.35 (6 H, br s, $CO_2H$); $^{13}$C NMR (DMSO-$d_6$) δ 166.42, 158.47, 137.21, 132.80, 126.45, 122.55, 119.36, 69.50; MS (negative FAB): 659 (found), 659 (M-1 calcd. for $C_{33}H_{24}O_{15}$).

Synthesis of 1,3,5-Tris{[3,5-bis(t-butyl 3,5-dibromosalicyloxycarbonyl)-phenoxy]methyl}benzene The hexacarboxylic acid from the previous step (0.05 g, 7.6×10$^{-5}$ mol), t-butyl 3,5-dibromosalicylate (0.18 g, 5.0×

$10^{-4}$ mol), 1-(3-dimethylaminopropyl)-3-ethylcarbodiimide hydrochloride (0.18 g, $9.1 \times 10^{-4}$ mol), and 4-dimethylaminopyridine (0.01 g, $10^{-4}$ mol) were dissolved in 8.0 mL of dry N,N-dimethylformamide, and the solution was stirred at 4° C. for 24 h. Ether, then water were added to the reaction mixture. The organic layer was separated and washed with water (in the cold room). The ethereal solution was dried over magnesium sulfate and filtered. Ether was removed and the product was dried in vacuum (white crystals, 0.18 g, 90%): $^1$H NMR (CDCl$_3$) δ 8.69 (3 H, t, J=1.3 Hz, ArH), 8.12 (6 H, d, J=1.3 Hz, ArH), 8.01 (6 H, d, J=2.0 Hz, ArH), 7.90 (6 H, d, J=2.0 Hz, ArH), 7.61 (3 H, s, ArH), 5.26 (6 H, s, CH$_2$), 1.36 (54 H, s, CH$_3$).

Synthesis of 1,3,5-Tris{[3,5-bis(3,5-dibromosalicyloxy-carbonyl)-phenoxy]methyl}benzene

Anhydrous trifluoroacetic acid (5.0 mL) was added to 0.18 g ($6.8 \times 10^{-5}$ mol) of the t-butyl protected compound produced in the previous step and the solution was allowed to stand under nitrogen at room temperature for 1 h. Dry ether (5.0 mL) was added, upon which the amount of white precipitate increased. It was filtered quickly and dried in vacuum.

REFERENCES

1. Collman et al., (1988) *J. Am. Chem. Soc.* 110, 3483
2. Kluger et al, (1992) *Biochemistry* 31, 7551
3. Kluger et al. *J. Am. Chem. Soc.* 114, 9275 (1992)
4. Jones et al. *Biochemistry* 32, 215 (1992)
5. Klotz et al. *Arch. Biochem. Biophys.* 1983, 228, 627
6. Vögtle et al., Chemische Berichte (1973), 106, 718

We claim:

1. A multifunctional crosslinking reagent for effecting chemical crosslinking of a hemoglobin and having at least four functional groups, two of said functional groups which react with the hemoglobin to effect crosslinking thereof, and another two of said functional groups which provide sites on the resultant crosslinked hemoglobin available for further reaction, said crosslinking reagent corresponding to the general formula I:

where m is an integer of 4–12;
n is an integer of 1–5;
R represents an aromatic grouping selected from the group consisting of phenyl, naphthyl, biphenyl, binaphthyl, phenyl-alkylene-phenyl, naphthyl-alkylene-naphthyl, phenyl-polyether-phenyl and naphthyl-polyether-naphthyl in which the alkylene linkages & the polyether linkages are from 2–20 atoms in linear extent;
X represents a direct bond, an ethylene group or an —NH— group;
Y represents —O—, —S— or a direct bond;
and Z represents from one to five independently selected electronegative groups exhibiting positive Hammett sigma values, directly bonded to the phenyl ring.

2. The crosslinking reagent of claim 1 wherein Y in general formula I represents —O—.

3. The crosslinking reagent of claim 1 wherein Y in general formula I represents —O— and wherein Z in general formula I is selected from the group consisting of acetamido, acetoxy, acetyl, carbomethoxy, carboxy, halo, cyano, ethoxy, hydroxy, methanesulfonyl, methoxy, nitro, phenyl, trifluoromethyl, trimethylammonio, phosphate, sulfonate, sulfate and diphosphinate.

4. The crosslinking reagent of claim 3 wherein integer n in general formula I is 2 or 3.

5. The crosslinking reagent of claim 4 wherein Z in general formula I is selected from the group consisting of carboxyl, phosponate, sulfonate, sulfate, phosphinate and halogen.

6. The crosslinking reagent of claim 5 wherein the group in general formula I is 3,5-dibromosalicyl.

7. The crosslinking reagent of claim 6 which is 3,5,3', 5'-biphenyltetracarbonyl tetrakis (3,5-dibromo-salicylate).

8. The crosslinking reagent of claim 6 which is 1,2-bis{2-[3, 5-bis(3,5-dibromosalicyloxy carbonyl)-phenoxy] ethoxy}ethane.

9. The crosslinking reagent of claim 6 which is 1,3,5-tris{[3,5-bis(3,5 -dibromosalicyloxy carbonyl)phenoxy]methyl}benzene.

10. A process of preparing crosslinked hemoglobin to produce a crosslinked hemoglobin having a plurality of free functionalities available for further chemical reaction and derived from the residue of the crosslinking reagent, which comprises reacting hemoglobin with a crosslinking reagent as defined in claim 1.

11. The process of claim 10 wherein the hemoglobin is human hemoglobin.

12. The process of claim 11 wherein the hemoglobin is reacted with the crosslinking reagent in its deoxy form.

13. The process of claim 11 wherein the crosslinking reagent is 3,5,3',5'-biphenyltetracarbonyl tetrakis-(3,5-dibromosalicylate).

14. The process of claim 11 wherein the crosslinking reagent is 1,2-bis{2-[3,5-bis(3,5-salicyloxy carbonyl) phenoxy]ethoxy}ethane.

15. A hemoglobin-biomolecule conjugate comprising a crosslinked hemoglobin having a crosslinking reagent residue covalently bonded thereto and being derived from a crosslinking reagent as defined in claim 1, said crosslinking reagent residue providing at least two reactive sites, and at least one biomolecule covalently bonded to a reactive site of the crosslinking reagent residue.

16. The hemoglobin-biomolecule conjugate of claim 15 wherein the hemoglobin is human hemoglobin.

17. The hemoglobin-biomolecule conjugate of claim 15 wherein the biomolecules are bonded to the crosslinking reagent residue utilizing primary or secondary amine groups on the biomolecules.

18. The hemoglobin-biomolecule conjugate of claim 15 wherein the biomolecule is selected from the groups consisting of amino acids, polyhydroxylamines, peptides, enzyme cofactor analogs, hormones, haptens, co-enzymes, nucleophilic group-containing drugs, saccharides, lipids and nucleic acids.

* * * * *